United States Patent
Kikuchi et al.

(10) Patent No.: US 9,017,959 B2
(45) Date of Patent: Apr. 28, 2015

(54) 5.9 KDA PEPTIDE IMMUNOASSAY METHOD

(75) Inventors: Wataru Kikuchi, Koriyama (JP); Momoe Sato, Koriyama (JP); Kenta Noda, Koriyama (JP); Iwao Kiyokawa, Koriyama (JP); Toshihide Miura, Koriyama (JP); Ryo Kojima, Koriyama (JP); Fumio Nomura, Chiba (JP); Kazuyuki Sogawa, Chiba (JP)

(73) Assignee: Nitto Boseki Co., Ltd., Fukushima (JP)

( * ) Notice: Subject to any disclaimer, the term of this patent is extended or adjusted under 35 U.S.C. 154(b) by 0 days.

(21) Appl. No.: 13/502,198

(22) PCT Filed: Oct. 13, 2010

(86) PCT No.: PCT/JP2010/067956
§ 371 (c)(1),
(2), (4) Date: Apr. 16, 2012

(87) PCT Pub. No.: WO2011/052380
PCT Pub. Date: May 5, 2011

(65) Prior Publication Data
US 2012/0276562 A1    Nov. 1, 2012

(30) Foreign Application Priority Data
Oct. 28, 2009   (JP) .................................. 2009-247332

(51) Int. Cl.
*G01N 33/53* (2006.01)
*G01N 33/543* (2006.01)
*G01N 33/68* (2006.01)
*C07K 16/36* (2006.01)

(52) U.S. Cl.
CPC ............ *G01N 33/6893* (2013.01); *C07K 16/36* (2013.01); *C07K 2317/34* (2013.01); *G01N 33/5308* (2013.01); *G01N 2333/75* (2013.01); *G01N 2800/08* (2013.01)

(58) Field of Classification Search
CPC .................. A61K 38/363; A61K 2039/55516; A61K 35/407; A61K 39/00; A61K 39/0011; C07K 14/75; C07K 14/4748; C12N 15/86; C12N 2710/14143; C12N 7/00; C12N 2830/008; C12N 2750/14143; C12N 2710/14121
See application file for complete search history.

(56) References Cited

U.S. PATENT DOCUMENTS 7,517,951 B2 *  4/2009  Nomura et al. ............... 530/324
7,611,855 B2   11/2009  Ohashi et al.
7,781,180 B2 *  8/2010  Nomura et al. ................ 435/7.1
2002/0182660 A1  12/2002  Fong
2003/0100035 A1   5/2003  Vojdani
2005/0069967 A1 *  3/2005  Sumida et al. .............. 435/7.92
2008/0286814 A1 * 11/2008  Lopez et al. ................. 435/7.23

FOREIGN PATENT DOCUMENTS

| CN | 1732385 A | 2/2006 | |
| EP | 1 577 385 A1 | 9/2005 | |
| WO | 2004/058966 | 7/2004 | |
| WO | WO2004/090550 | * 10/2004 | ............. G01N 33/68 |
| WO | 2007/053589 A2 | 5/2007 | |
| WO | 2008/105215 A1 | 9/2008 | |
| WO | WO2008/105215 | * 4/2009 | ............. G01N 33/68 |
| WO | 2009/088022 | 7/2009 | |

OTHER PUBLICATIONS

Extended European Search Report dated Jun. 6, 2013, in the corresponding European application No. 10826514.
Japanese Office Action dated Apr. 11, 2014, in the corresponding Japanese patent application No. 2011-538339, with a partial English translation.
Nakano, Masayuki, "ASH 3. Clinical Conditions and Pathological Diagnosis," Journal of Japanese Society of Internal Medicine, vol. 95, No. 1 (2006), pp. 28-32, with a translation of the Abstract.
Nomura, Fumio, et al., "Application of proteomic technologies to discover and identify biomarkers for excessive alcohol consumption: A review," Journal of Chromatography B, No. 855 (2007), pp. 35-41.
Hanash, Samir M., et al., "Mining the plasma proteome for cancer biomarkers," Nature, vol. 452 (2008), pp. 571-579.
Nomura, Fumio, et al., "Identification of novel and downregulated biomarkers for alcoholism by surface enhanced laser desorption/ionization-mass spectrometry," Proteomics (2004), No. 4, pp. 1187-1194.
Sogawa, Kazuyuki, et al., "Diagnostic Values of Surface-Enhanced laser Desorption/Ionization Technology for Screening of Habitual Drinkers," Alcoholism; Clinical and Experimental Research, vol. 31, No. S1 (Jan. 2007), pp. 22S-26S.
International Search Report mailed Nov. 22, 2010, in International Application No. PCT/JP2010/067956.

* cited by examiner

*Primary Examiner* — Christine Foster
*Assistant Examiner* — Carmencita M Belei
(74) *Attorney, Agent, or Firm* — Kratz, Quintos & Hanson, LLP (57) ABSTRACT

Disclosed is an immunoassay method whereby a 5.9 kDa peptide which results from the degradation of the α-E chain and α chain of human fibrinogens and which is used as a peptide marker for diagnosing hepatic disease can be specifically assayed in a biological sample containing contaminating peptides by bringing antibodies that recognize the N terminal of said peptide marker and antibodies that recognize the C terminal of said peptide marker into contact with said peptide marker, forming immune complexes of said peptide marker and the two antibodies, and immunoassaying the obtained immune complexes.

10 Claims, 2 Drawing Sheets

```
                        SEQUENCE LISTING

<160> NUMBER OF SEQ ID NOS: 6

<210> SEQ ID NO 1
<211> LENGTH: 54
<212> TYPE: PRT
<213> ORGANISM: Homo sapiens

<400> SEQUENCE: 1

Ser Ser Ser Tyr Ser Lys Gln Phe Thr Ser Ser Thr Ser Tyr Asn Arg
1               5                   10                  15

Gly Asp Ser Thr Phe Glu Ser Lys Ser Tyr Lys Met Ala Asp Glu Ala
            20                  25                  30

Gly Ser Glu Ala Asp His Glu Gly Thr His Ser Thr Lys Arg Gly His
        35                  40                  45

Ala Lys Ser Arg Pro Val
    50

<210> SEQ ID NO 2
<211> LENGTH: 18
<212> TYPE: PRT
<213> ORGANISM: Artificial Sequence
<220> FEATURE:
<223> OTHER INFORMATION: synthetic peptide

<400> SEQUENCE: 2

Ser Ser Ser Tyr Ser Lys Gln Phe Thr Ser Ser Thr Ser Tyr Asn Arg
1               5                   10                  15

Gly Cys

<210> SEQ ID NO 3
<211> LENGTH: 16
<212> TYPE: PRT
<213> ORGANISM: Artificial Sequence
<220> FEATURE:
<223> OTHER INFORMATION: synthetic peptide

<400> SEQUENCE: 3

Cys Gly Thr His Ser Thr Lys Arg Gly His Ala Lys Ser Arg Pro Val
1               5                   10                  15

<210> SEQ ID NO 4
<211> LENGTH: 7
<212> TYPE: PRT
<213> ORGANISM: Artificial Sequence
<220> FEATURE:
```

```
<223> OTHER INFORMATION: partial sequence

<400> SEQUENCE: 4

Glu Phe Pro Ser Arg Gly Lys
1               5

<210> SEQ ID NO 5
<211> LENGTH: 13
<212> TYPE: PRT
<213> ORGANISM: Artificial Sequence
<220> FEATURE:
<223> OTHER INFORMATION: partial sequence

<400> SEQUENCE: 5

Arg Asp Cys Asp Asp Val Leu Gln Thr His Pro Ser Gly
1               5                   10

<210> SEQ ID NO 6
<211> LENGTH: 13
<212> TYPE: PRT
<213> ORGANISM: Artificial Sequence
<220> FEATURE:
<223> OTHER INFORMATION: partial sequence

<400> SEQUENCE: 6

Arg Gly Ile His Thr Ser Pro Leu Gly Lys Pro Ser Leu
1               5                   10
```

5.9 KDA PEPTIDE IMMUNOASSAY METHOD

TECHNICAL FIELD

The present invention relates to a method of immunoassay for detecting a peptide of a molecular weight of 5,900 having an amino acid sequence as shown in SEQ ID NO: 1 (hereinafter referred to as 5.9 kDa peptide) as a degradation product of human fibrinogen α-E chain or human fibrinogen α chain, found to be usable as a peptide marker for hepatic disease by proteome analysis, from a sample or quantitating the concentration of the 5.9 kDa peptide in the sample, and an immunoassay kit therefor. The present invention also relates to an antibody recognizing an N-terminal region of the 5.9 kDa peptide and an antibody recognizing a C-terminal region thereof used in the method of immunoassay for a 5.9 kDa peptide.

INCORPORATION BY REFERENCE OF SEQUENCE LISTING

Applicant hereby incorporates by reference the electronically filed sequence listing, which is computer-readable file "W5787-01 SequenceListing.txt." This file was created on Jun. 28, 2012, and is of size 1240 bytes.

BACKGROUND ART

In recent years, exhaustive proteome analysis has progressed on a worldwide scale, and searches for disease markers using the proteome analysis have widely taken place (Patent Literatures 1 to 2 and Non Patent Literatures 1 to 3). In the proteome analysis, generally, a protein contained in a sample of biological origin or a peptide as its degradation product is isolated; the amino acid sequence of the isolated protein or peptide is analyzed using a mass spectrometer; the resultant amino acid sequence is compared with amino acid sequences in a database; and thereby the protein or the peptide contained in the sample is identified. Because proteins expressed in vivo differ by the presence or absence of disease, the protein or the peptide found to increase or decrease in expression level in a disease-specific manner by the proteome analysis has potential to be able to be used as a marker for the disease.

Through the proteome analysis, the present inventors identified the 5.9 kDa peptide as one of new serum peptides increasing or decreasing with the habit of drinking from serum samples collected with time from an alcoholic patient hospitalized for the purpose of abstinence and found that this can be used as a diagnosis marker for hepatic disease (Patent Literature 1 and Non Patent Literatures 1 to 2).

The present inventors showed that two monoclonal antibodies obtained using the MI-length 5.9 kDa peptide consisting of 54 residues as an antigen can be used to perform the immunoassay of the isolated 5.9 kDa peptide (Patent Literature 1).

CITATION LIST

Patent Literature

Patent Literature 1: International Publication No. WO 2004/058966
Patent Literature 2: International Publication No. WO 2004/090550

Non Patent Literature

Non Patent Literature 1: Nomura, F. et al., Proteomics, 4, 1187-1194, 2004
Non Patent Literature 2: Nomura, F. et al., J. Chromatogr. B., 855, 35-41, 2007
Non Patent Literature 3: Hanash, S. M. et al., Nature, 452, 571-579, 2008

SUMMARY OF INVENTION

Technical Problem

Many clinically useful peptides have so far been reported which were found using proteome analysis. However, to the present inventors' knowledge, there are almost no reports in which these candidate peptides as disease markers are quantitatively assayed using an immunological detection method widely commonly used in the field of clinical diagnosis. Difficulty in the establishment of a method of immunoassay therefor has hampered the spread of peptide markers discovered using proteome analysis.

First, the cause of the difficulty in the establishment of a method of immunoassay therefor involves the fact that it is difficult to produce a specific antibody for a peptide. Second, it involves the fact that a peptide discovered by proteome analysis is also often a degradation product of a mature protein present in a sample of biological origin and many degradation products other than a desired peptide each containing the sequence of the desired peptide sequence are mixed therewith in the sample. In such a case, even though an antibody is produced using the desired peptide as an immunogen, it gives rise to non-specific reactions with mixed degradation products, and thus the desired peptide cannot be exactly quantitatively analyzed.

Particularly, human fibrinogen from which the 5.9 kDa peptide to be assayed according to the present invention is produced by degradation is a protein involved in the coagulation/fibrinogenolysis system, and therefore many degradation products thereof are present in vivo. Specifically, fibrinogen is degraded by thrombin in the coagulation system to produce a fibrin monomer. In the fibrinogenolysis system, a fibrin polymer comprised of fibrin monomers is degraded at a plurality of sites thereof by plasmin; thus, many fibrinogen degradation products are formed inevitably.

For example, according to build Human Plasma Peptide-Atlas 2009-05 in the database PeptideAtlas (http://www.peptideatlas.org/), 239 peptides are observed as degradation products of human fibrinogen α-E chain (protein name in the database: ENSP00000306361).

As described above, the present inventors succeeded in preparing two monoclonal antibodies to the full-length 5.9 kDa peptide consisting of 54 residues using the 5.9 kDa peptide as an antigen and in immunoassaying the isolated 5.9 kDa peptide (Patent Literature 1). However, even when these monoclonal antibodies are used, they are found to admit of further improvement for sufficiently exactly and quantitatively assaying the 5.9 kDa peptide in a sample potentially containing many human fibrinogen degradation products.

With the foregoing circumstances in view, an object of the present invention is to provide a method of immunoassay for specifically detecting and quantitating the 5.9 kDa peptide from a sample potentially containing many human fibrinogen α-E chain/α chain degradation products. Another object of the present invention is to provide a kit for use in the method of immunoassay, and an antibody recognizing an N-terminal region of the 5.9 kDa peptide and an antibody recognizing a C-terminal region thereof used in the method of immunoassay and the kit.

Solution to Problem

Two types of fibrinogen chains containing the amino acid sequence of the 5.9 kDa peptide are known. Specifically, they are human fibrinogen α-E chain (hereinafter sometimes referred to as Fα-E chain) and human fibrinogen α chain (hereinafter sometimes referred to as Fα chain). Fα-E chain and Fα chain completely agree with each other in the amino acid sequence of the N-terminal upstream region relative to the sequence of the 5.9 kDa peptide but are different in the amino acid sequence of the C-terminal downstream region. As described above, degradation products of Fα-E chain and Fα chain are present as at least 200 or more contaminating peptides besides the 5.9 kDa peptide in a blood sample.

Thus, the present inventors initially attempted to produce a plurality of antibodies using a plurality of peptides having several amino acid sequences in Fα-E chain and Fα chain as antigens and assay the 5.9 kDa peptide using, among these, antibodies obtained employing regions nearest to the sequence of the 5.9 kDa peptide as antigens as antibodies for removing contaminating peptides and using the remaining as antibodies for assaying the 5.9 kDa peptide. In other words, the 5.9 kDa peptide in a sample was attempted to be assayed using the antibody for assaying the 5.9 kDa peptide after the operation of removing contaminating peptides using a plurality of antibodies for removing contaminating peptides.

Specifically, the antigen peptides used for preparing the antibodies for removing contaminating peptides were (a1) the 7-amino acid sequence (amino acid sequence: EFPSRGK (SEQ ID NO. 4)) of the N-terminal upstream region of the 5.9 kDa peptide region in Fα-E chain or Fα chain, (a2) an antibody recognizing the 13-amino acid sequence (amino acid sequence: RDCDDVLQTHPSG (SEQ ID NO. 5)) of the C-terminal downstream region of the 5.9 kDa peptide region in Fα-E chain, and (a3) the 13-amino acid sequence (amino acid sequence: RGIHTSPLGKPSL (SEQ ID NO. 6)) of the C-terminal downstream region of the 5.9 kDa peptide region in Fα chain. It was finally favorable to use (b1) an antibody recognizing the N-terminal region of the 5.9-kDa peptide and (b2) an antibody recognizing the C-terminal region of the 5.9 kDa peptide as antibodies for assaying the 5.9 kDa peptide.

However, the present inventors have surprisingly found that an immune complex of the 5.9 kDa peptide and two antibodies obtained by contacting the 5.9 kDa peptide, with the antibody recognizing the N-terminal region of the 5.9 kDa peptide and the antibody recognizing the C-terminal region of the 5.9 kDa peptide can be simply assayed without going through the above operation of removing contaminating peptides to substantially assay only the 5.9 kDa peptide from a sample potentially containing many human fibrinogen α-E chain/α chain degradation products without being affected by the contaminating peptides to be removed by the above contaminating peptide-removing operation despite that contaminating peptides to which the two antibodies bind are detected in the sample by a common western blotting method, thereby accomplishing the present invention.

Thus, the present invention relates to a method of immunoassay for a 5.9 kDa peptide in samples as cited below, a kit for the immunoassay, and antibodies used therefor.

[1] A method of immunoassay for a 5.9 kDa peptide, comprising contacting a peptide of a molecular weight of 5,900 having the amino acid sequence shown in SEQ ID NO. 1 (5.9 kDa peptide) in a sample, with an antibody or antibody fragment thereof recognizing an N-terminal region of the 5.9 kDa peptide and an antibody or antibody fragment thereof recognizing a C-terminal region of the 5.9 kDa peptide to form an immune complex of the 5.9 kDa peptide and the two antibodies or antibody fragments thereof and assaying the resultant immune complex.

[2] The method of immunoassay according to [1] above, wherein the antibody recognizing the N-terminal region of the 5.9 kDa peptide is an antibody recognizing any epitope present in a region of 1 to 39th amino acids from an N-terminal end of the 5.9 kDa peptide; the antibody recognizing the C-terminal region of the 5.9 kDa peptide is an antibody recognizing any epitope present in a region of 18 to 54th amino acids from the N-terminal end of the 5.9 kDa peptide and located towards a C-terminal end beyond the epitope recognized by the antibody recognizing the N-terminal region; and the epitopes recognized by these two antibodies do not overlap with each other and these two antibodies do not mutually interfere with binding to the 5.9 kDa peptide.

[3] The method of immunoassay according to [1] or [2] above, wherein the antibody recognizing the N-terminal region of the 5.9 kDa peptide is an antibody recognizing an epitope present in a region of 1 to 17th amino acids from the N-terminal end of the 5.9 kDa peptide.

[4] The method of immunoassay according to any of [1] to [3] above, wherein the antibody recognizing the C-terminal region of the 5.9 kDa peptide is an antibody recognizing an epitope present in a region of 40 to 54th amino acids from the N-terminal end of the 5.9 kDa peptide.

[5] The method of immunoassay according to any of [1] to [4] above, wherein the immune complex is assayed by a sandwich ELISA method.

[6] The method of immunoassay according to any of [1] to [4] above, wherein the immune complex is assayed by a latex immunoagglutination assay.

[7] The method of immunoassay according to any of [1] to [6] above, wherein the sample is whole blood, serum, plasma, urine, saliva, cerebrospinal fluid, pleural effusion, ascites, cardiac effusion, joint fluid, or lymph fluid and has potential to contain the 5.9 kDa peptide.

[8] A kit for immunoassay for a 5.9 kDa peptide, comprising an antibody or antibody fragment thereof recognizing an N-terminal region of the 5.9 kDa peptide and an antibody or antibody fragment thereof recognizing a C-terminal region of the 5.9 kDa peptide.

[9] The kit for immunoassay according to [8] above for assaying the 5.9 kDa peptide by a sandwich ELISA method, comprising the antibody or antibody fragment recognizing the N-terminal region of the 5.9 kDa peptide and the antibody or antibody fragment recognizing the C-terminal region of the 5.9 kDa peptide, wherein either of the antibodies or antibody fragments is a labeled antibody or a labeled antibody fragment and the other antibody or antibody fragment is a solid phase-bound antibody or a solid phase-bound antibody fragment.

[10] The kit for immunoassay according to [8] above for assaying the 5.9 kDa peptide by a latex immunoagglutination assay, comprising an insoluble carrier particle sensitized with an antibody or antibody fragment thereof recognizing the N-terminal region of the 5.9 kDa peptide and an insoluble carrier particle sensitized with an antibody or antibody fragment thereof recognizing the C-terminal region of the 5.9 kDa peptide.

[11] The kit for immunoassay according to [10] above, comprising an insoluble carrier particle obtained by sensitizing the particle with both two of the antibody or antibody fragment recognizing the N-terminal region of the 5.9 kDa peptide and the antibody or antibody fragment recognizing the C-terminal region of the 5.9 kDa peptide; two insoluble carrier particles obtained by sensitizing each of the two particles with either of the antibodies or antibody fragments and the other antibody or antibody fragment separately; or a mixture of these three insoluble carrier particles.

[12] An antibody or antibody fragment thereof recognizing an epitope present in a region of 1 to 17th amino acids from an N-terminal end of a 5.9 kDa peptide.

[13] An antibody or antibody fragment thereof recognizing an epitope present in a region of 40 to 54th amino acids from an N-terminal end of a 5.9 kDa peptide.

Advantageous Effects of Invention

The method of immunoassay for a 5.9 kDa peptide according to the present invention can specifically assay the 5.9 kDa peptide simply and exactly from a sample potentially containing many contaminating peptides. Although the quantitative assay of the 5.9 kDa peptide using a mass spectrometer is also possible, the 5.9 kDa peptide as a peptide marker for hepatic disease diagnosis can be quantitated using the method of immunoassay for a 5.9 kDa peptide according to the present invention, having more simplicity, comparable accuracy, and high throughput to easily perform diagnose the possibility for a habitual drinker or a problem drinker to develop hepatic disease, or a hepatic disease caused by other than drinking, for example, hepatitis, hepatic cirrhosis, or fatty liver.

DESCRIPTION OF EMBODIMENTS

The 5.9 kDa peptide assayed by the method of immunoassay for a 5.9 kDa peptide and the kit for immunoassay according to the present invention is a peptide having the amino acid sequence consisting of 54 amino acid residues shown in SEQ ID NO: 1 and having a theoretical molecular weight of 5,904.2. The peptide is present in the region of 576 to 629th amino acids from an N-terminal end of human fibrinogen α-E chain and human fibrinogen α chain, and is produced by the degradation of human fibrinogen α-E chain and human fibrinogen α chain.

The 5.9 kDa peptide assayed by the method of immunoassay for a 5.9 kDa peptide and the kit for immunoassay according to the present invention is a peptide marker for hepatic disease diagnosis, whose amount detected from a sample of biological origin decreases with a cause such as the habit of drinking.

The sample amenable to the method of immunoassay for a 5.9 kDa peptide according to the present invention is not particularly limited provided that it is a sample of biological origin potentially containing the 5.9 kDa peptide; examples thereof include various body fluids and cell tissue extracts; preferred is a body fluid collected from a patient suspected of hepatic disease in view of the function of the 5.9 kDa as a clinical marker and the simplicity of sample collection. Here, examples of the body fluid include whole blood, serum, plasma, urine, saliva, lymph fluid, cerebrospinal fluid, or punctured fluids including ascites, pleural effusion, cardiac effusion, and joint fluid; among others, particularly preferred are blood-derived samples having high potential to contain fibrinogen and fibrin involved in the coagulation/fibrinogenolysis system and multiple degradation products including the 5.9 kDa peptide produced from these proteins, that is, whole blood, plasma, and serum. Especially, the serum collected from a patient suspected of hepatic disease is preferable as a sample to be assayed by the method of immunoassay for a 5.9 kDa peptide according to the present invention.

The antibody recognizing an N-terminal region of the 5.9 kDa peptide and the antibody recognizing a C-terminal region of the 5.9 kDa peptide used in the method of immunoassay for a 5.9 kDa peptide and the kit for immunoassay according to the present invention are antibodies recognizing epitopes not overlapping with each other among several epitopes that may be present in the 5.9 kDa peptide and not mutually interfering with binding to the 5.9 kDa peptide. Here, the epitope recognized by the antibody recognizing the N-terminal region of the 5.9 kDa peptide used in the present invention is present towards the N-terminal end beyond the epitope recognized by the antibody recognizing the C-terminal region of the 5.9 kDa peptide used in the present invention.

Here, the antibody recognizing, the N-terminal region of the 5.9 kDa peptide and the antibody recognizing the C-terminal region of the 5.9 kDa peptide used in the method of immunoassay for a 5.9 kDa peptide and the kit for immunoassay according to the present invention may each be a monoclonal antibody or a polyclonal antibody provided that they enable immunoassay specific for the 5.9 kDa peptide. The isotypes of the antibodies are each not particularly limited; examples thereof include IgG1, IgG2, IgG3, IgG4, IgA1, IgA2, IgD, IgE, and IgM isotype antibodies; and IgG type antibodies are preferable in view of ease of antibody purification. The production method/production organism for obtaining the antibodies is not particularly limited either; examples thereof include the production of the antibodies using a mouse-derived hybridoma cell line.

For the antibody recognizing the N-terminal region of the 5.9 kDa peptide and the antibody recognizing the C-terminal region of the 5.9 kDa peptide used in the method of immunoassay for a 5.9 kDa peptide and the kit for immunoassay according to the present invention, the epitope refers to an amino acid region consisting typically of about 6 to 11 amino acid residues present on the molecular surface of an antigen, as a particular structural unit of the antigen which the antibody recognizes and binds to. Typically, one antigen has a plurality of epitopes.

For the antibody recognizing the N-terminal region of the 5.9 kDa peptide and the antibody recognizing the C-terminal region of the 5.9 kDa peptide used in the method of immunoassay for a 5.9 kDa peptide and the kit for immunoassay according to the present invention, that the two antibodies do not mutually interfering with binding to the 5.9 kDa peptide refers to not resulting in that the binding of one antibody to the 5.9 kDa peptide obstructs the binding of the other antibody thereto, for example, in a mode that when one antibody recognizes and binds to an epitope in the 5.9 kDa peptide, the antibody sterically covers all or part of an epitope recognized by the other antibody to inhibit the epitope recognition of the other antibody or that when the other antibody recognizes and binds to the epitope, the two antibodies contact each other.

Here, the spacing which two non-overlapping epitopes in the antigen should have for the antibodies recognizing the non-overlapping epitopes not to mutually obstruct the binding of either of antigens depends on the steric structure which the antigen can assume; however, there is preferably an amino acid region consisting of 6 or more residues, more preferably an amino acid region consisting of 20 or more residues, between the two epitopes; and more preferably, an amino acid region assuming a β turn structure is contained in the amino acid region between the two epitopes. The presence of a degree of spacing between the two epitopes reduces a possibility that the two antibodies are steric hindrances to each other. In addition, a β turn structure in which a peptide chain formed by 4 amino acid residues sharply turns is present between the two non-overlapping epitopes to reduce a possibility that the antibodies recognizing the respective epitopes contact each other.

As described in detail in Examples, since it has been determined that an epitope is present in the region of 1 to 17th or 40 to 54th amino acids from the N-terminal end of the amino acid sequence of the 5.9 kDa peptide shown in SEQ ID NO: 1, the antibody recognizing the N-terminal region of the 5.9 kDa peptide used in the method of immunoassay for a 5.9 kDa peptide and the kit for immunoassay according to the present invention is preferably an antibody recognizing any epitope present in the region of 1 to 39th amino acids from the N-terminal end of the amino acid sequence of the 5.9 kDa peptide shown in SEQ ID NO: 1, more preferably an antibody recognizing any epitope present in the region of 1 to 17th amino acids from the N-terminal end of the amino acid sequence of the 5.9 kDa peptide shown in SEQ ID NO: 1.

The antibody recognizing the C-terminal region of the 5.9 kDa peptide used in the method of immunoassay for a 5.9 kDa peptide and the kit for immunoassay according to the present invention is preferably an antibody recognizing an epitope present in the region of 18 to 54th amino acids from the N-terminal end of the amino acid sequence of the 5.9 kDa peptide shown in SEQ ID NO: 1 and located towards the C-terminal end beyond the epitope recognized by the antibody recognizing the N-terminal region of the 5.9 kDa peptide, more preferably an antibody recognizing an epitope present in the region of 40 to 54th amino acids from the N-terminal end of the amino acid sequence of the 5.9 kDa peptide shown in SEQ ID NO: 1.

Examples of the antibody recognizing an epitope present in the region of 1 to 17th or 40 to 54th amino acids from the N-terminal end of the 5.9 kDa peptide used in the method of immunoassay for a 5.9 kDa peptide and the kit for immunoassay according to the present invention or provided by the present invention include an antibody obtained using a peptide comprising the sequence of 1 to 17th or 40 to 54th amino acids from the N-terminal end of the amino acid sequence of the 5.9 kDa peptide shown in SEQ ID NO: 1 or a peptide in which one or several amino acids have at least one mutation selected from deletion, substitution, addition, or insertion in the amino acid sequence and which has an amino acid sequence comprising consecutive 90% or more of the amino acid sequence, as an antigen, or an antibody obtained using a complex obtained by binding the peptide used as an antigen to a carrier, as an immunogen.

Here, the peptide used as an antigen can be obtained, for example, by chemical synthesis using a known peptide synthesis technique.

The above carrier may use a known carrier such as keyhole limpet hemocyanin (KLH), bovine serum albumin (BSA), human serum albumin (HSA), fowl serum albumin, poly-L-lysine, polyalanyl lysine, dipalmityl lysine, tetanus toxoid, or polysaccharide. Here, methods for binding the peptide used as an antigen to a carrier can include, for example, an MBS (maleimidebenzoyloxy succinimide) method which involves binding the peptide used as an antigen to the carrier by the aid of the SH group of a Cys residue contained in the peptide used as an antigen or artificially introduced into the peptide used as an antigen.

The antibodies recognizing epitopes present in the regions of 1 to 17th and 40 to 54th amino acids from the N-terminal end of the 5.9 kDa peptide used in the method of immunoassay for a 5.9 kDa peptide and the kit for immunoassay according to the present invention or provided by the present invention may be monoclonal antibodies or polyclonal antibodies.

The antibody recognizing an epitope present in the region of 1 to 17th amino acids from the N-terminal end of the 5.9 kDa peptide used in the method of immunoassay for a 5.9 kDa peptide and the kit for immunoassay according to the present invention or provided by the present invention is preferably an antibody obtained using, as an immunogen, a complex of the carrier and a peptide in which a Cys residue used for binding an antigen peptide to the carrier is introduced into the N-terminal or C-terminal end of an antigen peptide comprising the sequence of 1 to 17th amino acids from the N-terminal end of the amino acid sequence of the 5.9 kDa peptide shown in SEQ ID NO: 1, more preferably an antibody obtained using, as an immunogen, a complex of KLH as a carrier and a peptide in which a Cys residue used for binding an antigen peptide to the carrier is introduced into the C-terminal end of the antigen peptide, that is, a peptide having the amino acid sequence shown in SEQ ID NO: 2, particularly preferably, a monoclonal antibody produced by hybridoma 5.9N-06 (International Accession No. NITE BP-797) established by the present inventors.

The antibody recognizing an epitope present in the region of 40 to 54th amino acids from the N-terminal end of the 5.9 kDa peptide used in the method of immunoassay for a 5.9 kDa peptide and the kit for immunoassay according to the present invention or provided by the present invention is preferably an antibody obtained using, as an immunogen, a complex of the carrier and a peptide in which a Cys residue used for binding an antigen peptide to the carrier is introduced into the N-terminal or C-terminal end of an antigen peptide comprising the sequence of 40 to 54th amino acids from the N-terminal end of the amino acid sequence of the 5.9 kDa peptide shown in SEQ ID NO: 1, more preferably an antibody obtained using, as an immunogen, a complex of KLH as a carrier and a peptide in which a Cys residue used for binding an antigen peptide to the carrier is introduced into the N-terminal end of the antigen peptide, that is, a peptide having the amino acid sequence shown in SEQ ID NO: 3, particularly preferably, a monoclonal antibody produced by hybridoma 5.9C-02 (International Accession No. NITE BP-798) established by the present inventors.

In the method of immunoassay for a 5.9 kDa peptide and the kit for immunoassay according to the present invention, antibody fragment thereof recognizing the N-terminal region of the 5.9 kDa peptide and antibody fragment thereof recognizing the C-terminal region of the 5.9 kDa peptide can be similarly used as long as they recognize the epitopes recognized by the respective antibodies. For the antibody recognizing an epitope present in the region of 1 to 17th amino acids from the N-terminal end of the 5.9 kDa peptide or the antibody recognizing an epitope present in the region of 40 to 54th amino acids from the N-terminal end of the 5.9 kDa peptide provided by the present invention, the antibody fragments thereof are also similarly provided as long as they recognize the epitopes recognized by the respective antibodies.

These antibody fragments are not particularly limited. Specific examples thereof include Fab, Fab', F(ab')$_2$, scFv, Diabody, dsFV, and a peptide comprising a complementarity determining region (hereinafter sometimes referred to as CDR).

Fab is an antibody fragment obtained by treating an IgG type antibody with a protease, papain, which has the approximate N-terminal half of an H chain and a whole L chain bound through a disulfide (S—S) bond and has a specific binding capacity to an antigen having a molecular weight of about 50,000 Da. According to the present invention, Fab can be obtained, for example, by treating the antibody recognizing an epitope present in the region of 1 to 17th amino acids from the N-terminal end of the 5.9 kDa peptide or the antibody recognizing an epitope present in the region of 40 to 54th amino acids from the N-terminal end of the 5.9 kDa peptide provided by the present invention with the protease papain.

F(ab')$_2$ is an antibody fragment obtained by treating an IgG type antibody with a protease, pepsin, which is somewhat larger than one in which Fabs are bound through the S—S bond in a hinge region and has a specific binding capacity to an antigen having a molecular weight of about 100,000 Da. According to the present invention, F(ab')$_2$ can be obtained, for example, by treating the antibody recognizing an epitope present in the region of 1 to 17th amino acids from the N-terminal end of the 5.9 kDa peptide or the antibody recognizing an epitope present in the region of 40 to 54th amino acids from the N-terminal end of the 5.9 kDa peptide provided by the present invention with the protease pepsin. Alternatively, it can be prepared by subjecting the following Fab's to thioether bond or S—S bond.

Fab' is an antibody fragment obtained by breaking the S—S bond in the hinge region of the above F(ab')$_2$, which has a specific binding capacity to an antigen having a molecular weight of about 50,000 Da. According to the present invention, it may be obtained by treating F(ab')$_2$ with a reducing agent, dithiothreitol.

scFv is a VH-P-VL or VL-P-VH polypeptide obtained by linking a variable region of one H chain (VH) to a variable region of one L chain (VL) using a suitable peptide linker (P) having 12 residues or more and is an antibody fragment having a specific binding capacity to an antigen.

Diabody is an antibody fragment in which scFVs having the same or different antigen-binding specificities form a dimer and which has higher reactivity to the same antigen than that of scFv or has the same specific binding capacity to different antigens as that thereof.

dsFv is obtained by substituting one amino acid residue in each of the variable region of the H chain and the variable region of the L chain with a Cys residue and binding the resultant polypeptides together through the S—S bond between the Cys residues.

The peptide comprising CDR is formed by containing at least one region or more of CDR of the variable region of the H chain or the variable region of the L chain. The peptide comprising a plurality of CDRs can be produced by binding them together directly or through a suitable peptide linker.

Various antibodies used in the method of immunoassay for a 5.9 kDa peptide and the kit for immunoassay according to the present invention or provided by the present invention can each be prepared or obtained, after immunizing an animal using an antigen therefor, for example, a 5.9 kDa peptide fragment containing the epitope recognized by the respective antibody, a variant thereof, the full-length 5.9 kDa peptide, a variant of the full-length 5.9 kDa peptide, or a complex of each of the peptides and the above carrier as an immunogen, by a known method from the serum of the animal for a polyclonal antibody or through recovery and purification from the hybridoma obtained by fusing antibody-producing cells derived from the spleen or the like of the animal and myeloma cells.

Here, the peptide used as an immunogen may be obtained by purification from a sample of biological origin such as human blood; however, it may also be obtained by chemical synthesis using a known peptide synthesis technique. Without being limited to these, a peptide produced by a recombinant technique may also be used as an antigen.

The hybridoma producing any of various antibodies used in the method of immunoassay for a 5.9 kDa peptide and the kit for immunoassay according to the present invention or provided by the present invention can be prepared by a known method, for example, the method of Kohler and Milstein (Kohler, G. & Milstein, C. Nature, 256, 495-497, 1975). Specifically, the above immunogen is mixed with a known adjuvant; then, the prepared adjuvant solution is immunized to an animal to be immunized such as a mouse, a rat, a hamster, or a goat as many times as required at an interval and an increase in the antibody titer is confirmed; and thereafter, antibody-producing cells derived from the spleen or the like of the animal are fused with myeloma cells of a mammal such as a mouse or a rat to prepare a hybridoma.

The above hybridoma 5.9N-06 producing an antibody recognizing an epitope present in the region of 1 to 17th amino acids from the N-terminal end of the 5.9 kDa peptide used in the method of immunoassay for a 5.9 kDa peptide and the kit for immunoassay according to the present invention or provided by the present invention and the above hybridoma 5.9C-02 producing an antibody recognizing an epitope present in the region of 40 to 54th amino acids from the C-terminal end of the 5.9 kDa peptide used in the method of immunoassay for a 5.9 kDa peptide and the kit for immunoassay according to the present invention or provided by the present invention, both prepared and established by the present inventors, were deposited in National Institute of Technology and Evaluation (NITE), Patent Microorganisms Depositary (NPMD), 2-5-8 Kazusakamatari, Kisarazu-shi, Chiba 292-0818, Japan, on Aug. 19, 2009, and have been assigned the accession numbers NITE P-797 and NITE P-798, respectively. Thereafter, requests were made for conversion of these deposits into international deposits under the Budapest Treaty, as of Aug. 20, 2010, and they have been given the International Accession numbers NITE BP-797 and NITE BP-798, respectively, as of Sep. 13, 2010.

To obtain, from hybridomas, various monoclonal antibodies used in the method of immunoassay for a 5.9 kDa peptide and the kit for immunoassay according to the present invention or provided by the present invention, the prepared hybridomas are first selected using a selection medium, followed by analyzing the culture supernatant of the selected hybridomas by a suitable immunoassay method such as an ELISA method to select a hybridoma producing a desired monoclonal antibody. Then, the selected clone is cloned by a method such as a limiting dilution method for monoclonalization. Subsequently, the cloned hybridoma can be cultured in a medium commonly used for cell culture, for example, α-MEM, RPMI1640, ASF, or S-clone, followed by recovering a monoclonal antibody from the culture supernatant. An animal from which the hybridoma is derived, a nude mouse, may also be treated with pristane in advance, followed by causing ascites fluid to accumulate by intraperitoneally injecting the cells into the animal before recovering a monoclonal antibody from the ascites fluid. Finally, the method for recovering the monoclonal antibody from the supernatant or the ascites fluid may use a conventional method. Examples thereof include a salting-out method using ammonium sulfate, sodium sulfate, or the like, chromatography, ion-exchange chromatography, and affinity chromatography typically using protein G.

Various antibodies or antibody fragments used in the method of immunoassay for a 5.9 kDa peptide and the kit for immunoassay according to the present invention or provided by the present invention can also be obtained by analyzing the DNA sequence encoding each of these antibodies or fragments by a known method, then, preparing a recombinant vector containing the DNA sequence, introducing the prepared recombinant vector into a suitable host, for example, *Escherichia coli* or yeast, and recovering the antibody or the antibody fragment from the resultant recombinant before purification.

The immune complex generated in the method of immunoassay for a 5.9 kDa peptide according to the present invention is a complex of the 5.9 kDa peptide and two antibodies or antibody fragments, formed by the simultaneous contact/binding of both the antibody or antibody fragment thereof recognizing the N-terminal end of the 5.9 kDa peptide and the antibody or antibody fragment thereof recognizing the C-terminal end of the 5.9 kDa peptide used in the method of immunoassay for a 5.9 kDa peptide and the kit for immunoassay according to the present invention or provided by the present invention with the 5.9 kDa peptide, or by the contact/binding of a complex of the 5.9 kDa peptide with one of the antibodies or antibody fragments formed by the contact/binding of the 5.9 kDa peptide and the antibody or the antibody fragment and further with the other antibody or antibody fragment thereof. Here, the formed complex may be a trimer or larger multimer.

In the immune complex generated in the method of immunoassay for a 5.9 kDa peptide according to the present invention, one of the antibody or antibody fragment thereof recognizing the N-terminal end of the 5.9 kDa peptide and the antibody or antibody fragment thereof recognizing the C-terminal end of the 5.9 kDa peptide used in the method of immunoassay for a 5.9 kDa peptide and the kit for immunoassay according to the present invention or provided by the present invention, forming the complex, may bind to a solid phase, that is, a base material using a raw material such as polystyrene, polypropylene, polycarbonate, polyethylene, nylon, or polymethacrylate, for example, a plastic tube or a microtiter plate by use of direct or indirect, physical or chemical binding, affinity, or the like in a mode of maintaining their antigen-recognizing ability. The other antibody or antibody fragment thereof not binding to the solid phase may be labeled with a marker, for example, a marker enzyme such as HRP, a marker metal such as colloidal gold or europium, any of various chemical or biological fluorescent substances such as FTTC, rhodamine, Texas Red, Alexa, or GFP, or a radioactive substance such as $^{32}$P or $^{51}$Cr in a mode of maintaining their antigen-recognizing ability.

Alternatively, in the immune complex generated in the method of immunoassay for a 5.9 kDa peptide according to the present invention, both of the antibody or antibody fragment thereof recognizing the N-terminal end of the 5.9 kDa peptide and the antibody or antibody fragment thereof recognizing the C-terminal end of the 5.9 kDa peptide used in the method of immunoassay for a 5.9 kDa peptide and the kit for immunoassay according to the present invention or provided by the present invention may bind to insoluble carrier particles, for example, a latex of an organic polymer such as polystyrene or styrene-butadiene copolymer, an inorganic oxide such as silica, alumina, or the like by use of direct or indirect, physical or chemical binding, affinity, or the like in a mode of maintaining their antigen-recognizing ability.

Means for assaying the immune complex generated in the method of immunoassay for a 5.9 kDa peptide according to the present invention can include, for example, an enzyme-linked immunosorbent assay method (ELISA method), a turbidimetric immunoassay method (TIA method), a latex immunoagglutination assay method (LATEX method), an electrochemiluminescence method, and a fluorescence method. An immunochromatography method and a method using a test paper are also useful.

The mean for assaying the immune complex generated in the method of immunoassay for a 5.9 kDa peptide according to the present invention is preferably an ELISA method, more preferably a sandwich ELISA method in view of having excellent sensitivity and quantitativity.

The mean for assaying the immune complex generated in the method of immunoassay for a 5.9 kDa peptide according to the present invention is also preferably a latex immunoagglutination assay in view of being simple and rapid.

The assay by a sandwich ELISA method performed in the method of immunoassay for a 5.9 kDa peptide according to the present invention uses a labeled antibody or a labeled antibody fragment in which one of the antibody or antibody fragment thereof recognizing the N-terminal end of the 5.9 kDa peptide and the antibody or antibody fragment thereof recognizing the C-terminal end of the 5.9 kDa peptide used in the method of immunoassay for a 5.9 kDa peptide and the kit for immunoassay according to the present invention or provided by the present invention is labeled with a marker, for example, a marker enzyme such as HRP, a marker metal such as colloidal gold or europium, any of various chemical or biological fluorescent substances such as FTTC, rhodamine, Texas Red, Alexa, or GFP, or a radioactive substance such as $^{32}$P or $^{51}$Cr in a mode of maintaining their antigen-recognizing ability. In addition, the assay by a sandwich ELISA method performed in the method of immunoassay for a 5.9 kDa peptide according to the present invention uses a solid phase-bound antibody or a solid phase-bound antibody fragment in which the other antibody or the antibody fragment not used in the above labeled antibody or the labeled antibody fragment binds to a solid phase, that is, a base material using a raw material such as polystyrene, polypropylene, polycarbonate, polyethylene, nylon, or polymethacrylate, for example, a plastic tube or a microtiter plate by use of direct or indirect, physical or chemical binding, affinity, or the like in a mode of maintaining their antigen-recognizing ability.

The assay by a sandwich ELISA method performed in the method of immunoassay for a 5.9 kDa peptide according to the present invention can be carried out by a known method using the labeled antibody or the labeled antibody fragment and the solid phase-bound antibody or the solid phase-bound antibody fragment. Specifically, a sample is first added to the solid phase-bound antibody or the solid phase-bound antibody fragment for reaction; after reaction for a set time, the solid phase is washed; and the labeled antibody or the labeled antibody fragment is further added thereto for a second-order reaction. Then, the solid phase is again washed, and a chromogenic substrate or the like is added for reaction. Here, the chromogenic substrate may use DAB, TMB, or the like which is known when HRP is used as a marker for the labeled antibody or the labeled antibody fragment.

The kit for 5.9 kDa peptide immunoassay by a sandwich ELISA method provided by the present invention includes the labeled antibody or the labeled antibody fragment and the solid phase-bound antibody or the solid phase-bound antibody fragment used in the assay by a sandwich ELISA method performed in the method of immunoassay for a 5.9 kDa peptide according to the present invention. In addition, the kit for 5.9 kDa peptide immunoassay by a sandwich ELISA method provided by the present invention may comprise a substrate, a sample diluent, a wash solution, a positive control, a negative control, and the like. Here, to simply and rapidly assay many samples, it is preferably formed as an immunoassay kit enabling assay using an automated ELISA device.

The assay by a latex immunoagglutination assay performed in the method of immunoassay for a 5.9 kDa peptide according to the present invention uses insoluble carrier particles sensitized with the antibody or antibody fragment thereof recognizing the N-terminal end of the 5.9 kDa peptide and the antibody or antibody fragment thereof recognizing the C-terminal end of the 5.9 kDa peptide used in the method of immunoassay for a 5.9 kDa peptide and the kit for immunoassay according to the present invention or provided by the present invention. Here, the sensitization of insoluble carrier particles with the antibody or antibody fragment thereof refers to binding the antibody or antibody fragment thereof to the insoluble carrier particles by use of direct or indirect, physical or chemical binding, affinity, or the like in a mode of maintaining their antigen-recognizing ability. Examples of the insoluble carrier particles include a latex of an organic polymer such as polystyrene or styrene-butadiene copolymer and an inorganic oxide such as silica, alumina. As to the mode of using insoluble carrier particles sensitized with the two antibodies or antibody fragments, an insoluble carrier particle obtained by sensitizing the particle with both of the two antibodies or antibody fragments may be used, or a mixture of two insoluble carrier particles obtained by sensitizing each of the two particles with either of the antibodies or antibody fragments and the other antibody or antibody fragment separately may be used or a mixture of the three insoluble carrier particles may be used.

The assay by a latex immunoagglutination assay performed in the method of immunoassay for a 5.9 kDa peptide according to the present invention may be carried out by a known method using the two insoluble carrier particles. Specifically, the two insoluble carrier particles are added to a sample for reaction, and after reaction for a set time, the formed agglutination is assayed.

The kit for 5.9 kDa peptide immunoassay by a latex immunoagglutination assay provided by the present invention includes the antibody or antibody fragment thereof recognizing the N-terminal end of the 5.9 kDa peptide and the antibody or antibody fragment thereof recognizing the C-terminal end of the 5.9 kDa peptide sensitized to insoluble carrier particles used in the assay by a latex immunoagglutination assay performed in the method of immunoassay for a 5.9 kDa peptide according to the present invention. In addition, the kit for 5.9 kDa peptide immunoassay by a latex immunoagglutination assay provided by the present invention may comprise a sample diluent, a positive control, a negative control, and the like. Here, to simply and rapidly assay many samples, it is preferably formed as an immunoassay kit enabling assay using an automated latex immunoagglutination assay device.

The present invention will be described below in further detail with reference to Examples. However, this invention is not intended to be limited to these Examples in any manner.

Example 1

Preparation of Antibody Recognizing N-terminal Region of 5.9 kDa Peptide and Antibody Recognizing C-terminal Region of 5.9 kDa Peptide and Identification of Characteristic Thereof (1) Preparation of Immunogen To prepare an antibody recognizing an N-terminal region of a 5.9 kDa peptide and an antibody recognizing a C-terminal region of the 5.9 kDa peptide, an immunogen was prepared which comprises a peptide comprising an N-terminal or C-terminal amino acid sequence of the 5.9 kDa peptide.

Specifically, at the C-terminal end of an antigen peptide consisting of 17 amino acid residues, of 1 to 17th amino acid residues from the N-terminal end of the amino acid sequence of the 5.9 kDa peptide shown in SEQ ID NO: 1 (hereinafter referred to as 5.9 N) was first synthesized a peptide in which a Cys residue used for binding the antigen peptide to a carrier was introduced, that is, a peptide having the amino acid sequence shown in SEQ ID NO: 2. At the N-terminal end of an antigen peptide consisting of 15 contiguous residues from the C-terminal end of the 5.9 kDa peptide, that is, consisting of 15 amino acid residues, of 40 to 54th amino acid residues from the N-terminal end of the amino acid sequence of the 5.9 kDa peptide shown in SEQ ID NO: 1 (hereinafter referred to as 5.9 C) was also synthesized a peptide in which a Cys residue used for binding the antigen peptide to the carrier was introduced, that is, a peptide having the amino acid sequence shown in SEQ ID NO: 3.

Then, keyhole limpet hemocyanin (KLH) as a carrier was conjugated to the N-terminal Cys residue or C-terminal Cys residue of these peptides by an MBS (maleimidebenzoyloxy succinimide) method to prepare a complex used as an immunogen.

(2) Immunization of Mouse

The immunogen obtained in (1) above was administered to mice to provide immunized mice.

Specifically, the immunogen comprising 5.9 N or 5.9 C prepared in (1) above was first dissolved in PBS to 1 mg/ml. Then, 50 µl (50 µg) thereof was taken, and well mixed to emulsification with 50 µl of Freund's complete adjuvant (Wako Pure Chemical Industries). Subsequently, each prepared suspension was intraperitoneally administered to 6-week-old Balb/c6 female mice (Clea Japan, Inc.) under diethyl ether anesthesia. After 2 weeks, the same amount of the immunogen comprising 5.9 N or 5.9 C was mixed with Freund's incomplete adjuvant (Wako Pure Chemical Industries) to make an emulsified suspension by just the same operation as that for Freund's complete adjuvant, and the suspension was administered to mice. Thereafter, the same operation was performed every two weeks, and in the fourth round, 50 µl (50 µg) of the immunogen comprising 5.9 N or 5.9 C was administered to mice by tail vein injection for final immunization.

(3) Establishment of Hybridoma

Spleen cells of the immunized mice obtained in (2) above were fused with myeloma cells to prepare hybridomas.

Specifically, 3 days after the final immunization of the immunogen comprising 5.9 N or 5.9 C, the spleen surgically removed from each mouse under diethyl ether anesthesia was first aseptically dispersed to prepare spleen cells. The cell fusion was carried out according to the method of Kohler and Milstein (Kohler, G & Milstein, C. Nature, 256, 495-497, 1975); the spleen cells were fused with the myeloma cells P3-X63-Ag8-U1 (P3U1) using polyethylene glycol (PEG4000) (Merck). The fusion ratio was $8\times10^7$ spleen cells to $2\times10^7$ myeloma cells (P3-X63-Ag8-U1 (P3U1)) and about 4:1. The fused cells were dispersed in a 10% FCS (INVITROGEN) α-MEM (IRVINE) HAT (Cosmo Bio) medium, which was then dispensed into a 96-well microtiter culture plate (Sumitomo Bakelite) and cultured under conditions of 37° C. and 5% $CO_2$.

(4) Screening of Colony

About 2 weeks after the hybridoma establishment of (3) above, the growth of colonies was confirmed and hybridomas producing the antibodies were selected through screening.

Specifically, to prepare a plate for screening, the 5.9 N or 5.9 C synthesized in (1) above was first dissolved in PBS, which was then dispensed into a 96-well microtiter plate (Nunc) to 2 μg/100 μl/well. Next, the plate was allowed to stand at 4° C. for two nights, and then washed three times with PBS containing 0.05% Tween 20 (PBS-T) (Wako Pure Chemical Industries); to inhibit non-specific reaction, 200 μl of an N-102 (NOF Corporation) solution diluted 4-fold in PBS was dispensed thereinto, which was further allowed to stand at 4° C. overnight. Subsequently, after washing the completed plate once with PBS-T, 100 μl of the culture supernatant of the hybridoma obtained in (3) above was reacted therewith; after further washing, an HRP-labeled anti-mouse immunoglobulin antibody (Zymed) as a secondary antibody was added thereto for reaction. After washing, 100 μl of a TMB solution (Kainos) as a chromogenic substrate for HRP was added thereto and color-developed for a set time, followed by further adding 100 μl of 1N sulfuric acid (Wako Pure Chemical Industries) as a stop solution thereto and assaying absorbance at an assay wavelength of 450 nm.

Clones determined to be positive through the above screening were each re-cloned by a limiting dilution method, and the supernatant was again confirmed.

As a result, a hybridoma, 5.9 N-06, reacting with the plate sensitized with 5.9 N and a hybridoma, 5.9 C-02, reacting with the plate sensitized with 5.9 C were obtained. The culture supernatant of each of the hybridomas obtained completely failed to react with a BSA plate as a control.

The hybridomas 5.9 N-06 and 5.9 C-02 were deposited in National Institute of Technology and Evaluation (NITE), Patent Microorganisms Depositary (NPMD), 2-5-8 Kazusakamatari, Kisarazu-shi, Chiba 292-0818, Japan, on Aug. 19, 2009, and have been assigned the accession numbers NITE P-797 and NITE P-798, respectively. Thereafter, requests were made for conversion of these deposits into international deposits under the Budapest Treaty, as of Aug. 20, 2010, and they have been given the International Accession numbers NITE BP-797 and NITE BP-798, respectively, as of Sep. 13, 2010.

(5) Isotype Identification of Antibody

The isotypes of monoclonal antibodies, anti-5.9 N and anti-5.9 C, produced by the hybridoma 5.9 N-06 and the hybridoma 5.9 C-02, respectively, obtained in (4) above were identified.

Specifically, the isotype of the antibody produced by each hybridoma was checked using a monoclonal antibody-typing kit (Amersham Pharmacia) according to the appended instructions.

As a result, the monoclonal antibodies anti-5.9 N and anti-5.9 C were determined to belong to the isotype shown in Table 1.

TABLE 1

Isotype of Monoclonal Antibody

| Monoclonal Antibody Name | Antibody Class | Antibody Subclass | Light Chain Type |
|---|---|---|---|
| anti-5.9 N | IgG | IgG1 | κ |
| anti-5.9 C | IgG | IgG1 | κ |

(6) Purification of Antibody

The culture supernatants of the hybridoma 5.9 N-06 and the hybridoma 5.9 C-02 were purified using Protein G Sepharose Fast Flow (GE Healthcare) according to the appended instructions to provide the monoclonal antibodies anti-5.9 N and anti-5.9 C.

Example 2

Construction of 5.9 kDa Peptide Assay System Using ELISA Method and Assay of 5.9 kDa Peptide in Specimen (1) Confirmation of Reactivity of Antibody with 5.9 kDa Peptide by Western Blotting Method Using a western blotting method, the two antibodies binding to the N-terminal and C-terminal ends of the 5.9 kDa peptide prepared in Example 1 were confirmed to bind to the full-length 5.9 kDa peptide by a method as specifically described below.

(1-1) SDS-PAGE/Blotting

Under non-reduction, 0.5 μg each of aliquots of the synthesized 5.9 kDa peptide was subjected to SDS-PAGE. Thereafter, they were each transferred to PVDF membrane (Millipore) and subjected to blocking for 1 hour.

(1-2) Primary Antibody Response

The two antibodies (a PBS-T containing 0.05 mg/ml of anti-5.9 N and a PBS-T containing 0.005 mg/ml of anti-5.9 C) purified in (6) of Example 1 were each reacted with the membrane having the 5.9 kDa peptide transferred thereto prepared in (1-1) above for 1 hour.

(1-3) Secondary Antibody Response

After washing the membrane with PBS-T, an HRP-labeled anti-mouse immunoglobulin antibody (Zymed) was reacted as a secondary antibody therewith for 30 minutes.

(1-4) Color Development

After washing with PBS-T, detection was carried out using a TMB solution for membranes (Wako Pure Chemical Industries).

(1-5) Result

Both the two antibodies prepared were confirmed to recognize the 5.9 kDa peptide.

(2) Construction of 5.9 kDa Peptide Assay System Using ELISA Method

A sandwich ELISA assay system was prepared which uses the antibodies prepared in Example 1, and it was confirmed by a method as specifically described below that an antigen-antibody reaction was assayed in a concentration-dependent manner by the prepared ELISA assay system.

(2-1) Preparation of Antibody-Bound Plate

A MaxiSorp plate (Nunc) was sensitized overnight with the monoclonal antibody anti-5.9 C purified in (6) of Example 1 in a concentration of 0.5 μg/100 μl/well. After washing 3 times with PBS, blocking was carried out using N-102 (NOF Corporation) diluted 5-fold in distilled water.

(2-2) Preparation of HRP-Labeled Antibody

The monoclonal antibody anti-5.9 N purified in (6) of Example 1 was HRP-labeled using Peroxidase Labeling Kit-NH$_2$ (Dojindo Molecular Technologies). Here, the labeled antibody concentration was set to 1 μg/μl.

(2-3) Evaluation of ELISA Assay System

The effectiveness of the sandwich ELISA assay system was evaluated using the plate and the labeled antibody prepared in (2-2) above.

The serum used as a sample was used by being anonymized in an unlinkable fashion after obtaining informed consent. The concentration of the 5.9 kDa peptide in the sample was calculated by an SI-MS method as described below.

The serum in which the concentration of the 5.9 kDa peptide contained was calculated by the SI-MS method was used as a sample and assayed using the sandwich assay system; as a result, it was determined that absorbance was increased in a manner dependent on the concentration of the 5.9 kDa peptide.

SI-MS Method

The concentration of the 5.9 kDa peptide in the sample was calculated using ClinProt™ system (Bruker Daltonics) in which magnetic beads and MALDI-TOF/TOF MS were combined.

Specifically, a certain amount of a stable isotope peptide (SI-5.9 kDa) corresponding to the 5.9 kDa peptide was first added as an internal standard to the serum. The resultant was then bound to cation-exchange magnetic beads (WCX) (Bruker Daltonics) and eluted. Subsequently, the eluted sample was directly adjusted for Anchor Chip (Bruker Daltonics) and then assayed using AutoFlex® II (MALDI-TOF/TOF).

Here, analysis was carried out by performing baseline correction and smoothing treatment using FlexAnalysis™ software 2.4 (Bruker Daltonics) and calculating the 5.9 kDa peptide concentration in the serum based on the amount of the SI-5.9 kDa added, from the ratio of the peak intensity corresponding to the SI-5.9 kDa to the peak intensity corresponding to the 5.9 kDa peptide in the serum.

(3) Assay of 5.9 kDa Peptide in Human Serum

The 5.9 kDa peptide in human serum was assayed using the sandwich ELISA assay system prepared in (2) above, and it was determined by a method as specifically described below that an antigen-antibody reaction was observed in a manner dependent on the 5.9 kDa peptide concentration.

The serum used was used by being anonymized in an unlinkable fashion after obtaining informed consent.

(3-1) Primary Antibody Response

The human serum in which the concentration of the 5.9 kDa peptide contained was calculated by the SI-MS method was diluted with PBS to prepare samples having 5.9 kDa peptide concentrations of 0 μg/ml, 0.65 μg/ml, 1.30 μg/ml, 3.89 μg/ml, 7.12 μg/ml, and 10.36 μg/ml. These samples were diluted 1/333 with PBS, and 100 μl each thereof was reacted with the antibody-bound plate prepared in (2-1) above for 1 hour.

(3-2) Secondary Antibody Response

The plate was washed three times with PBS-T and then reacted with the HRP-labeled antibody (one diluted 1/4,000 with PBS-T) prepared in (2-2) above for 30 minutes.

(3-3) Color Development

After washing the plate, 100 μl of a TMB solution (Kainos) as a chromogenic substrate for HRP was added and color-developed for a set time, followed by further adding 100 μl of 1N sulfuric acid (Wako Pure Chemical Industries) as a stop solution thereto and assaying absorbance at a assay wavelength of 450 nm.

(3-4) Assay

Absorbance assay was carried out at a wavelength of 450 nm using an assay microplate reader. A calibration curve obtained by the absorbance assay is shown in FIG. 1.

Figure 1:
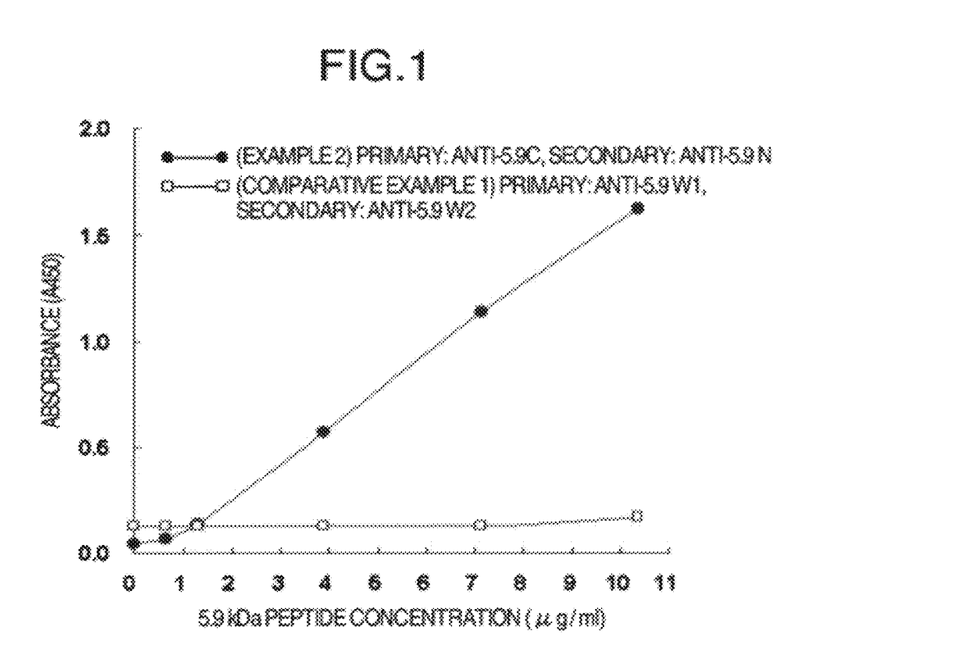
FIG. 1 is a graph showing a calibration curve when the concentration of a 5.9 kDa peptide in a serum is assayed using the sandwich ELISA assay system of the present invention using anti-5.9 C as a primary antibody and anti-5.9 N as a secondary antibody, prepared in Example 2 and the sandwich ELISA assay system using anti-5.9 W1 as a primary antibody and anti-5.9 W2 as a secondary antibody, prepared in Comparative Example 1. The vertical axis represents absorbance at a wavelength of 450 nm, and the horizontal axis represents the 5.9 kDa peptide concentration (μg/ml) before being diluted 1/333.

As shown in FIG. 1, the sandwich ELISA assay system using anti-5.9 N and anti-5.9 C detected the 5.9 kDa peptide contained in the serum with high sensitivity, confirming an increase, dependent on the 5.9 kDa peptide concentration, in absorbance.

Comparative Example 1

Assay of 5.9 kDa Peptide in Human Serum by ELISA Assay System Using Antibody Recognizing Full-Length 5.9 kDa Peptide The same assay as in (3) of Example 2 was carried out using a sandwich ELISA assay system constructed using an antibody recognizing the full-length 5.9 kDa peptide, anti-5.9 W1 (extracted and purified from the hybridoma CN-2 described in International Publication No. WO 2004/058966 (Accession Number: IPOD FERM BP-08565)), in place of anti-5.9 C in (2-1) of Example 2 and an antibody recognizing the full-length 5.9 kDa peptide, anti-5.9 W2 (extracted and purified from the hybridoma CN-1 described in International Publication No. WO 2004/058966 (Accession Number: IPOD FERM BP-08564)), in place of anti-5.9 N in (2-2) of Example 2.

A Calibration Curve Obtained by the Assay is Shown in FIG. 1.

As shown in FIG. 1, for the sandwich ELISA assay system using anti-5.9 W1 as a primary antibody and anti-5.9 W2 as a secondary antibody, an increase in absorbance was not observed, dependent on the concentration of the 5.9 kDa peptide contained in a low concentration in the serum.

In addition, the same behavior was also confirmed for a sandwich ELISA assay system using anti-5.9 W1 as a primary antibody and the monoclonal antibody anti-5.9 C of the present invention as a secondary antibody, a sandwich ELISA assay system using anti-5.9 W1 as a primary antibody and the monoclonal antibody anti-5.9 N of the present invention as a secondary antibody, and a sandwich ELISA assay system using the monoclonal antibody anti-5.9 C of the present invention as a primary antibody and 5.9 W2 as a secondary antibody.

Example 3

Confirmation of Correlation between SI-MS Method and ELISA Assay

The correlation was confirmed between the results of assay of the 5.9 kDa peptide concentration in the human serum by a quantitative essay method using the SI-MS method and the results of quantitative assay thereof using the ELISA assay system prepared in Example 2, determining that the ELISA assay system specifically quantitated the full-length 5.9 kDa peptide among many fibrinogen-related peptides contained in the serum.

The samples used were 8 serum samples obtained from healthy subjects and 8 serum samples obtained from alcoholic patients, and used by being anonymized in an unlinkable fashion after obtaining informed consents.

Specifically, using the ELISA assay system prepared in (3) of Example 2, the concentration of the 5.9 kDa peptide in the 16 serum samples in which the concentration of the 5.9 kDa peptide contained was calculated by the SI-MS method was quantitated based on the calibration curve prepared from the assay results of (3) of Example 2.

Figure 2:
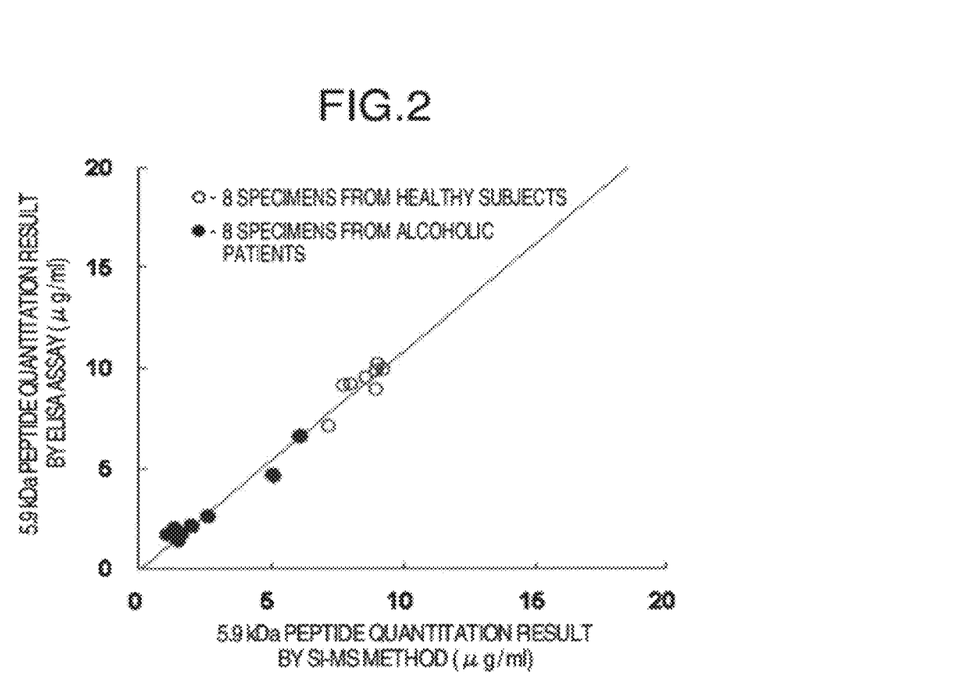
FIG. 2 is a graph showing the correlation between the results of quantitation of the 5.9 kDa peptide concentration in the same serum samples by the ELISA assay of the present invention and by an SI-MS method. The vertical axis represents the 5.9 kDa peptide concentration (μg/ml) assayed by the ELISA assay of the present invention, and the horizontal axis represents the 5.9 kDa peptide concentration (μg/ml) calculated by the SI-MS method. The white circles represent 8 serum samples obtained from healthy subjects and the black circles represent 8 serum samples obtained from alcoholic patients.

The results of the comparison between the results of quantitating the 5.9 kDa peptide based on the SI-MS method and the results of the quantitation based on the ELISA assay in the same samples are shown in FIG. 2.

As shown in FIG. 2, the quantitation results by the SI-MS method showed a clear correlation with the quantitation results by the ELISA assay. These results suggest that the sandwich ELISA system prepared in Example 2 specifically quantitates the 5.9 kDa peptide among many peptides present in the serum.

The 5.9 kDa peptide quantitation results by the ELISA assay could be completely separated in the 8 serum samples obtained from the healthy subjects and the 8 serum samples obtained from the alcoholic patients by applying the threshold value of 6.8 µg/ml. The 5.9 kDa peptide quantitation results by the ELISA assay showed a significant difference at a significance level of 1% or less by analysis of variance between the group consisting of the 8 serum samples obtained from the healthy subjects and the group consisting of the 8 serum samples obtained from the alcoholic patients.

Example 4

Construction of 5.9 kDa Peptide Assay System Using Latex Particle and Assay of 5.9 kDa Peptide in Specimen (1) Preparation of Latex Particle Sensitized to Anti-5.9 kDa Antibody.

Anti-5.9 kDa antibody-sensitized latex particles were prepared by preparing two types of latex particles to which the two monoclonal antibodies (anti-5.9 N and anti-5.9 C) prepared in Example 1 were bound and mixing the resultant particles, according to a method as specifically described below.

The reagent composition used here was as follows.

| BSA Coat Solution | |
| --- | --- |
| HEPES 2-[4-(2-hydroxyethyl)-1-piperazinyl]ethanesulfonic acid | 25 mM, pH 7.5 |
| Sodium Chloride | 150 mM |
| Disodium Ethylenediaminetetraacetate | 1.0 mM |
| Sodium Azide | 0.05% |
| Bovine Serum Albumin (BSA) | 1.0% |

| Buffer for Dilution | |
| --- | --- |
| HEPES | 25 mM pH 7.5 |
| Disodium Ethylenediaminetetraacetate | 1.0 mM |
| Sodium Azide | 0.05% |

| Buffer for Dispersion | |
| --- | --- |
| HEPES | 25 mM pH 7.5 |
| Sodium Chloride | 150 mM |
| Disodium Ethylenediaminetetraacetate | 1.0 mM |
| Sodium Azide | 0.05% |

(1-1) Preparation of Anti-5.9 N-Sensitized Latex Particle

To 100 ml of a solution of latex particles of 120 nm in diameter adjusted to a concentration of 1% using the buffer for dilution was added 100 ml of a solution in which anti-5.9 N was dissolved in the buffer for dilution to 3 mg/ml, which was then stirred at room temperature for 1 hour. Thereafter, the resultant was centrifuged at 20,000 rpm for 1 hour, followed by discarding the supernatant to recover the precipitate. To the precipitate was added 100 ml of the BSA coat solution to suspend the precipitate, and the suspension was completely dispersed by ultrasonication, followed by stirring at room temperature for 1 hour. Then, the resultant was centrifuged, and 500 ml of the buffer for dispersion was added to the resulting precipitate to suspend, which was then subjected to ultrasonication for complete dispersion to provide anti-5.9 N-sensitized latex particles in a concentration of 0.2%.

(1-2) Preparation of Anti-5.9 C-Sensitized Latex Particle

To 100 ml of a solution of latex particles of 120 nm in diameter adjusted to a concentration of 1% using the buffer for dilution was added 100 ml of a solution in which anti-5.9 C was dissolved in the buffer for dilution to 3 mg/ml, which was then stirred at room temperature for 1 hour. Thereafter, the resultant was centrifuged at 20,000 rpm for 1 hour, followed by discarding the supernatant to recover the precipitate. To the precipitate was added 100 ml of the BSA coat solution to suspend the precipitate, and the suspension was completely dispersed by ultrasonication, followed by stirring at room temperature for 1 hour. Then, the resultant was centrifuged, and 500 ml of the buffer for dispersion was added to the resulting precipitate to suspend, which was then subjected to ultrasonication for complete dispersion to provide anti-5.9 C-sensitized latex particles in a concentration of 0.2%.

(1-3) Preparation of Anti-5.9 kDa Antibody-Sensitized Latex Particle (LA Reagent)

A mixture of the latex particle solutions prepared in (1-1) and (1-2) above at a ratio of 1:1 was prepared as a second reagent for the LATEX method.

The buffer for dispersion was used as a first reagent for the LATEX method.

(2) Assay of 5.9 kDa Peptide in Human Serum

It was confirmed that the LA reagent prepared in (1-3) above could be used to quantitate the 5.9 kDa peptide in the human serum by latex immunoagglutination assay (LATEX assay).

Specifically, 100 µl of the first reagent and 100 µl of the second reagent were reacted with 10 µl of a human serum sample in which the concentration of the 5.9 kDa peptide contained was calculated using the SI-MS method, and the amount of change in absorbance was assayed by a two-point end method between 19 to 34 assay points (corresponding to from about 1 minute to 5 minutes after adding the second reagent) at a dominant wavelength of 570 nm and a secondary wavelength of 800 nm using Hitachi Model 7180 Autoanalyzer.

As a result, as shown in Table 2, an increase in absorbance dependent on the 5.9 kDa peptide concentration was confirmed.

TABLE 2

| 5.9 kDa Peptide Concentration (µg/ml) | Absorbance |
| --- | --- |
| 0.00 | −0.0080 |
| 2.59 | 0.0112 |
| 5.18 | 0.0393 |
| 10.36 | 0.1582 |

(3) Confirmation of Correlation between ELISA Assay and LATEX Assay

The correlation was confirmed between the ELISA assay suggested to specifically detect the 5.9 kDa peptide in the serum from the correlation with the SI-MS method in Example 3 and the LATEX assay, determining that the LATEX assay specifically detected the 5.9 kDa peptide in the serum.

Specifically, the 5.9 kDa peptide concentration in the serum was quantitated based on the calibration curve prepared from the assay results of (2) above. The 5.9 kDa peptide concentration in the same sample was quantitated by the ELISA assay as described in (2-3) of Example 3, and the correlation with the quantitation results by the LATEX assay are shown in FIG. 3.

Figure 3:
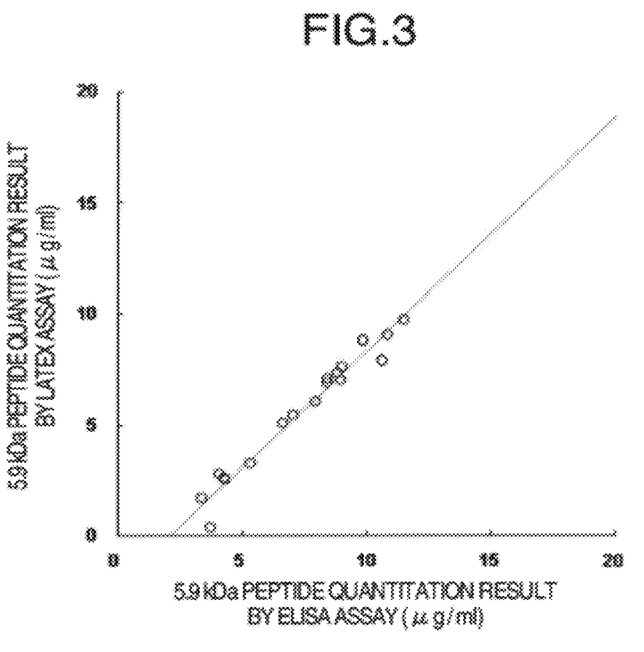
FIG. 3 is a graph showing the correlation between the results of quantitation of the 5.9 kDa peptide concentration in the same serum samples by the latex immunoagglutination assay (LATEX assay) of the present invention and by the ELISA assay of the present invention. The vertical axis represents the 5.9 kDa peptide concentration (μg/ml) assayed by the LATEX assay of the present invention, and the horizontal axis represents the 5.9 kDa peptide concentration (μg/ml) assayed by the ELISA assay of the present invention.

As a result, as shown in FIG. 3, the LATEX assay and the ELISA assay showed high correlation with each other, suggesting that the LATEX assay also specifically detected the 5.9 kDa peptide in the serum.

Industrial Applicability

The method of immunoassay for a 5.9 kDa peptide according to the present invention enables the simple and exact quantitation of the 5.9 kDa peptide as a peptide marker for hepatic disease diagnosis from a sample. The 5.9 kDa peptide can be used for the diagnosis of the possibility for a habitual drinker or a problem drinker to develop hepatic disease or the diagnosis of a hepatic disease caused by other than drinking, for example, hepatitis, hepatic cirrhosis, or fatty liver, and the method of immunoassay for a 5.9 kDa peptide according to the present invention is probably of high significance as a method for clinically diagnosing these diseases from a preventive medicine viewpoint, in view of current hepatic disease population.

SEQUENCE LISTING FREE TEXT

SEQ ID NO: 2: Description of Artificial Sequence: Synthetic Peptide

SEQ ID NO: 3: Description of Artificial Sequence: Synthetic Peptide

The invention claimed is:

1. A method of immunoassay for a peptide consisting of SEQ ID NO: 1, comprising:
   contacting a sample suspected of containing a mixture of peptides comprising the peptide consisting of SEQ ID NO: 1 and a peptide consisting of SEQ ID NO:4 fused to SEQ ID NO: 1, at the N-terminus of SEQ ID NO: 1, with an antibody or antibody fragment thereof recognizing the epitope of 1st to 17th amino acids of SEQ ID NO: 1 in the peptide of SEQ ID NO: 1, and with an antibody or antibody fragment thereof recognizing the epitope of 40th to 54th amino acids of SEQ ID NO: 1 so as to form an immune complex of the peptide of SEQ ID NO: 1 in the sample and the two antibodies or antibody fragments thereof; and
   detecting the resultant immune complex,
   wherein the antibody recognizing the epitope of 1st to 17th amino acids of SEQ ID NO: 1 is a monoclonal antibody produced by the hybridoma of International Accession Number NITE BP-797, and does not bind the peptide consisting of SEQ ID NO:4 fused to SEQ ID NO: 1, at the N-terminus of SEQ ID NO: 1.

2. The method of immunoassay according to claim 1, wherein the immune complex is detected by a sandwich ELISA method.

3. The method of immunoassay according to claim 1, wherein the immune complex is detected by a latex immunoagglutination assay.

4. The method of immunoassay according to claim 1, wherein the sample is whole blood, serum, plasma, urine, saliva, cerebrospinal fluid, pleural effusion, ascites, cardiac effusion, joint fluid, or lymph fluid.

5. The method of immunoassay according to claim 1, wherein:
   the antibody recognizing the the epitope of $40^{th}$ to $54^{th}$ amino acids of SEQ ID NO: 1 is a monoclonal antibody produced by the hybridoma of International Accession Number NITE BP-798.

6. A kit for immunoassay for a peptide of SEQ ID NO: 1, comprising an antibody or antibody fragment thereof recognizing the epitope of 1st to 17th amino acids of SEQ ID NO: 1 and an antibody or antibody fragment thereof recognizing the epitope of 40th to 54th amino acids of SEQ ID NO: 1,
   wherein the antibody recognizing the region of 1st to 17th amino acids of SEQ ID NO: 1 is a monoclonal antibody produced by the hybridoma of International Accession Number NITE BP-797, and does not bind the peptide consisting of SEQ ID NO:4 fused to SEQ ID NO: 1, at the N-terminus of SEQ ID NO: 1.

7. The kit for immunoassay according to claim 6 wherein either of the antibodies or antibody fragments is a labeled antibody or a labeled antibody fragment and the other antibody or antibody fragment is a solid phase-bound antibody or a solid phase-bound antibody fragment.

8. The kit for immunoassay according to claim 6, comprising an insoluble carrier particle sensitized with the antibody or antibody fragment thereof recognizing the epitope of $1^{st}$ to $17^{th}$ amino acids of SEQ ID NO: 1 and an insoluble carrier particle sensitized with the antibody or antibody fragment thereof recognizing the epitope of $40^{th}$ to $54^{th}$ amino acids of SEQ ID NO: 1.

9. The kit for immunoassay according to claim 8, comprising an insoluble carrier particle obtained by sensitizing the particle with the antibody or antibody fragment thereof recognizing the epitope of $1^{st}$ to $17^{th}$ amino acids of SEQ ID NO: 1 and the antibody or antibody fragment thereof recognizing the epitope of $40^{th}$ to $54^{th}$ amino acids of SEQ ID NO: 1; two insoluble carrier particles obtained by sensitizing each of the two particles with either of the antibodies or antibody fragments and the other antibody or antibody fragment separately; or a mixture of these three insoluble carrier particles.

10. The kit for immunoassay according to claim 6, wherein:

the antibody recognizing the epitope of 40$^{th}$ to 54$^{th}$ amino acids of SEQ ID NO: 1 is a monoclonal antibody produced by the hybridoma of International Accession Number NITE BP-798.

* * * * *